United States Patent [19]

Zeits et al.

[11] Patent Number: 4,459,258
[45] Date of Patent: Jul. 10, 1984

[54] ELEMENTAL ANALYZER AND METHOD

[75] Inventors: Alfred J. Zeits; Robert O. Canada, both of Wilmington, N.C.

[73] Assignee: General Electric Company, San Jose, Calif.

[21] Appl. No.: 294,542

[22] Filed: Aug. 20, 1981

[51] Int. Cl.³ .................. G21C 17/00; G01N 23/20
[52] U.S. Cl. ............................... 376/157; 376/257; 378/45; 378/48
[58] Field of Search .................. 376/157, 159, 257; 378/45, 48

[56] References Cited

U.S. PATENT DOCUMENTS

| 2,707,555 | 5/1955 | Gaudin | 376/157 |
| 3,247,380 | 4/1966 | Amiel et al. | 376/157 |
| 3,270,200 | 8/1966 | Rhodes | 378/48 |
| 3,445,651 | 5/1969 | Starnes | 376/157 |
| 3,562,525 | 2/1971 | Constantine et al. | 378/48 |
| 3,671,744 | 6/1972 | Constantine | 378/48 |
| 4,031,388 | 6/1977 | Morita et al. | 376/157 |
| 4,045,676 | 8/1977 | Rolle | 378/48 |
| 4,224,517 | 9/1980 | Lubecki et al. | 378/45 |
| 4,229,654 | 10/1980 | Arya et al. | 376/159 |

OTHER PUBLICATIONS

Anal. Chem, vol. 44, No. 14 (12/72) pp. 57A,58A,60A,63A,64A,66A,68A, Kneip et al.
Quantitative X-Ray Analysis, Zavodskaya Laboratoriya, vol. 40, No. 4, p. 408, Boechenin.
Nuc. Inst. J. Meth., 84(1970) pp. 141-143 Johansson et al. 3761157 X-Ray Analysis.
44

Primary Examiner—Sal Cangialosi
Attorney, Agent, or Firm—Ivor J. James, Jr.; Samuel E. Turner; Raymond G. Simkins

[57] ABSTRACT

A method and apparatus for analyzing combined secondary and primary materials by directing primary radiation onto said material whereby secondary radiation is generated. A detector senses the secondary radiation as a transport carries the materials into the vicinity of primary radiation and produces signals to be resolved into secondary and primary material source components, establishing a secondary to primary material ratio and indicating the composition of the material.

15 Claims, 13 Drawing Figures

CHART E

ELEMENTAL ANALYZER AND METHOD

BACKGROUND

The concentration of burnable neutron absorbers such as $Gd_2O_3$ in nuclear reactor fuels is a factor in determining core reactivity during reactor operation after fuel insertion into the core. Prediction of core reactivity is a safety parameter and it is also useful in efforts to optimize reactor performance and to minimize waste.

A conventional method of determining gadolinia content involves destructive testing. This involves essentially testing in a chemical laboratory. Unfortunately, this consumes a portion of the fuel examined. Furthermore, such tests are not capable of being performed "on site" where the fuel is actually manufactured, but necessitates moving fuel specimen to the laboratory itself, causing substantial time delays.

As performed by the instant invention, a non-destructive analysis is performed by x-ray fluorescence which, as is known to those familiar with the art, can be used to measure the concentrations of one or more secondary materials or elements in suitable matrices of elements of a primary material using methods such as those described in standard references such as *X-Ray Absorption and Emission in Analytical Chemistry* by H. A. Liebhafsky, H. G. Pfeiffer, E. H. Winslow, and P. D. Zemany (John Wiley & Sons, New York, 1960); *Practical X-Ray Spectrometry* by R. Jenkins and J. L. DeVries (Springer-Verlag, New York, 1967); *X-Ray Spectrochemical Analysis*, second edition, by L. S. Birks (Interscience, New York, 1969); and *Principles and Practice of X-Ray Spectrometric Analysis* by E. P. Bertin (Plenum Press, New York, 1970). In the instant invention, specimens are irradiated with primary radiation and secondary radiation of the elements of interest is detected and measured. In one embodiment, the secondary radiation response includes x-rays from K-band gadolinium electrons and L-band uranium electrons.

The secondary radiation varies as a result of environmental, including thermal, factors. Insofar as the x-ray response and counts are commonly affected, the common influence of environmental variations can be factored out by obtaining ratios of radiation from secondary materials including for example gadolinium to that of a primary material such as for example uranium, and determining concentrations of these secondary materials or elements from pre-established calibration curves according to the instant invention.

OBJECTS OF THE INVENTION

In manufacturing processes including for example the production of nuclear fuel, the material produced is in the form of powder or solid geometric bodies at various stages in manufacturing. Accordingly, an object of the instant invention is to provide a non-destructive analysis method that is able to accommodate both powder and solid forms of material.

Furthermore, many manufacturing facilities operate around the clock. It is accordingly an additional object of the instant invention to provide an x-ray fluorescence analyzer that is continually available - that is, on "STANDBY" twenty-four hours per day.

Another object of the present invention is to provide an x-ray fluorescence analyzer capable of self-monitoring and self-calibration.

Another object of the instant invention is to provide a relatively environmentally independent and thermally independent x-ray fluorescence analyzer.

SUMMARY OF THE INVENTION

The invention includes a method for analyzing the concentration of secondary materials or elements, such as gadolinium, in a matrix of the primary material, such as uranium dioxide nuclear fuel. A calibration curve is established to show the relationship of the ratio of the secondary element or material count response versus secondary element or material concentration.

In the embodiment shown the secondary material is gadolinium sesquioxide, $Gd_2O_3$, and the primary material is uranium dioxide, $UO_2$. Of course, other secondary and primary materials could be substituted in accordance with the knowledge of one skilled in the art.

The invention provides an apparatus or x-ray fluorescence analyzer which is capable of specimen analysis day or night - around the clock. While the apparatus is on STANDBY, it continually monitors certain physical conditions essential to performance (e.g., the level of liquid nitrogen needed to cool the detector crystal), and it further repeatedly monitors the validity of the calibration curve, and reestablishes it ab initio, if necessary.

The apparatus centers or positions each specimen including samples or standards at the detector site to establish the calibration curve, to check its validity, and to conduct specimen analysis.

DRAWING OF A PREFERRED EMBODIMENT

The invention will be better understood from the accompanying description of the preferred embodiment taken in conjunction with the accompanying drawing, wherein.

Figure 7:
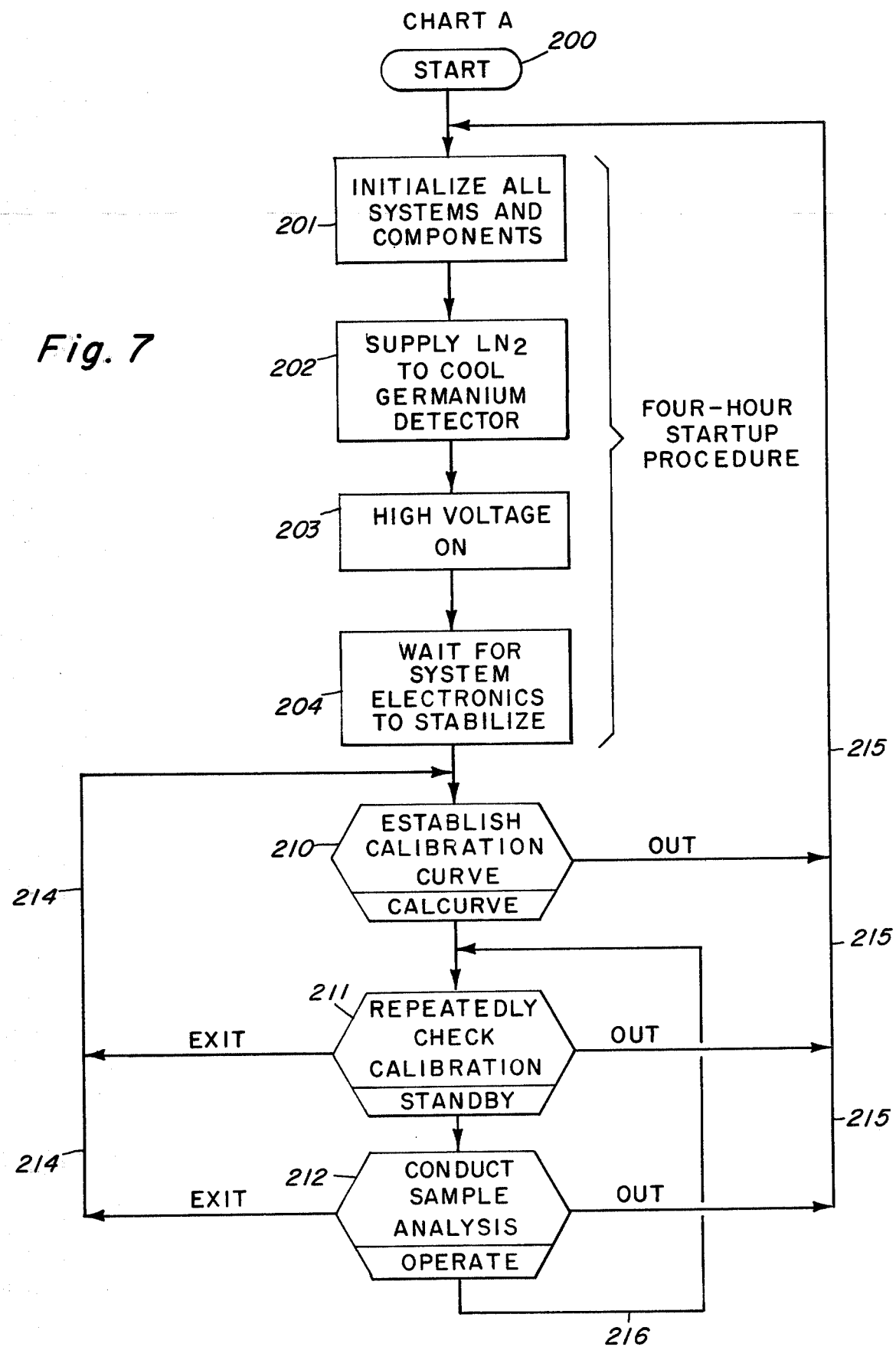
FIG. 7 is an overall flow chart of analyzer operation.
Figure 8:
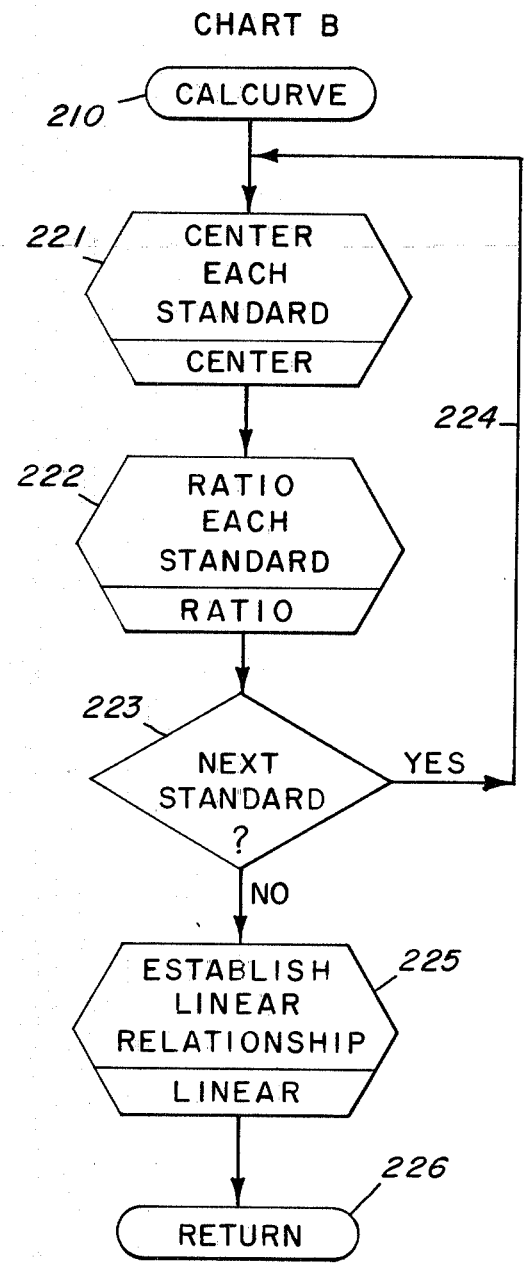

FIGS. 8 through 13 set forth details of operation of the analyzer, as generally set forth in FIG. 7.

DESCRIPTION OF THE PREFERRED EMBODIMENT

Figure 1:
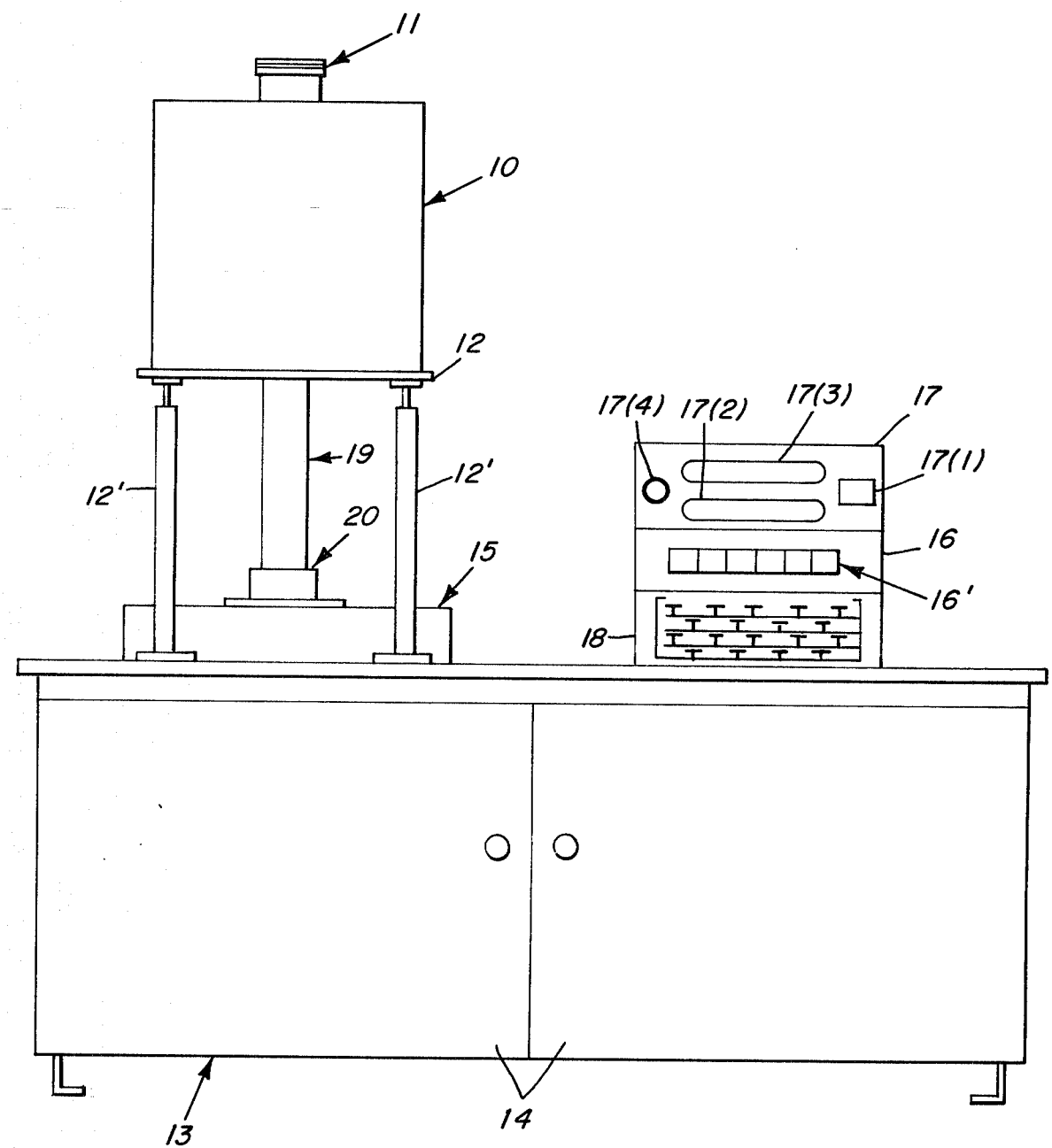
FIG. 1 is a frontal view of the x-ray fluorescence analyzer.

FIG. 1 shows a dewar assembly 10, including a liquid nitrogen refill mechanism 11, which is suitably mounted on a table 12 including legs 12' supported by a cabinet 13 having doors 14 suitably hinged mounted thereon.

On the cabinet 13 is a tray and transport housing 15; a control console 16 including switches 16'; a status module 17 including a printer 17 (1), a status indicator 17 (2), a display 17 (3), and a sonic alarm 17 (4); and a key board 18. Between the dewar assembly 10 and the tray and transport housing 15 is a detector assembly 19, and a source holder and shield 20.

Figure 2:
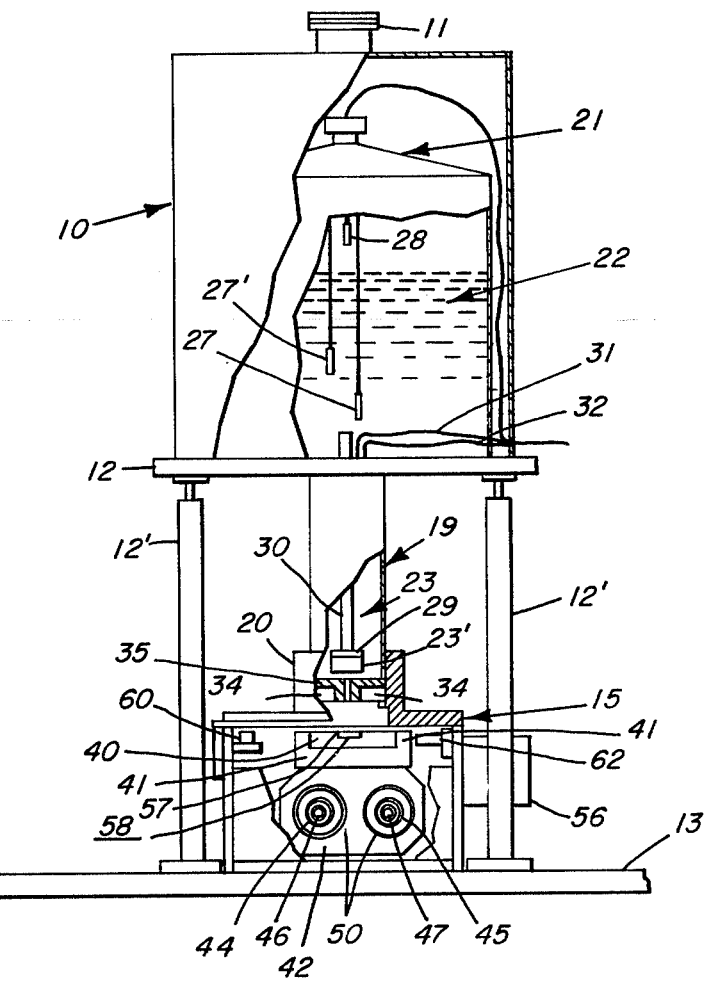
FIG. 2 is a side view of a partial cross-section of a portion of the analyzer, showing the detector and source of radiation.
Figure 3:
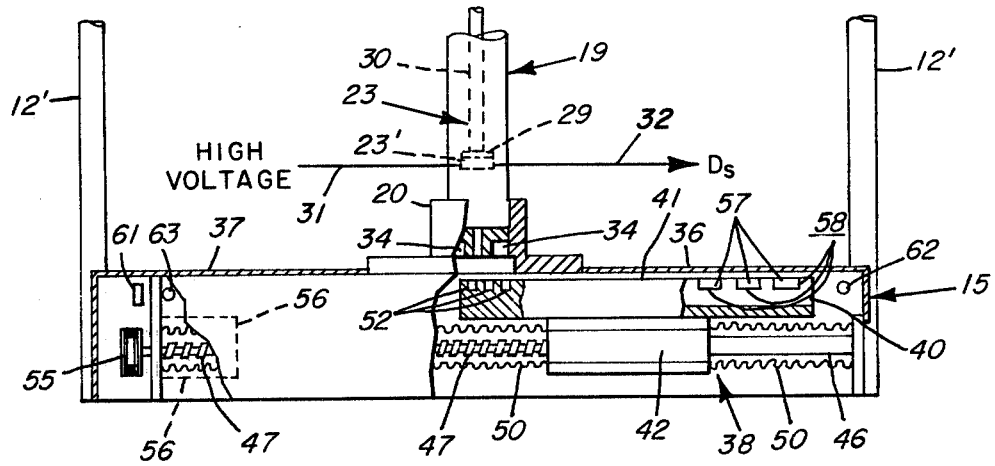
FIG. 3 is a broken-away view of the tray and transport housing of the analyzer, exhibiting the specimen transport system of the analyzer.

As shown in FIGS. 2 and 3, the dewar assembly 10 includes a dewar 21 which holds liquid nitrogen 22. The detector assembly 19 similarly includes a detector 23, which in turn includes a detector crystal 23' which is preferably an intrinsic germanium diode. The liquid nitrogen 22 cools the detector 23 by absorbing thermal energy produced during high-voltage operation.

The liquid nitrogen refilling mechanism 11 shown in FIG. 1 automatically replenishes the supply of liquid nitrogen 22 from a suitable source (not shown) when signaled by a suitable low-level detector 27'. Replenishment continues until stopped by a suitable signal from a high-level detector 28.

A vacuum is maintained within the detector assembly 19 to protect the detector crystal 23'. The detector 23 monitors the generation of secondary radiation produced in a specimen 57 and produces signals indicative of the source of secondary radiation—that is, whether the secondary radiation is derived from the primary material, uranium, or the secondary material, gadolinium. This secondary radiation is typically of the nature of x-ray radiation.

The detector crystal 23' is suitably mounted on an electric insulator 29 which in turn is mounted on the end of a cold finger 30, which is effective for removing thermal energy produced during operation.

High voltage is applied to the detector crystal from a source (not shown) along one of leads 31 in the dewar assembly 10. Another lead 32 carries source indicating signals $D_s$ from the detector 23 to the process controller system shown in FIG. 4.

A source 34 of primary radiation is suitably mounted in the source holder and shield 20, which protects the operator from undue radiation exposure. The source 34 is nominally a one-curie source and preferably is formed of concentric rings of americium 241, but other sources and configurations may be suitable. A collimator defines a suitable aperture (of dimensions, e.g., $10 \times 3.5$ mm dia) for admitting secondary radiation to the detector crystal. The collimator 35 is preferably made of tungsten material and eliminates unwanted scattered radiation, which improves detector resolution and precision by establishing a suitable field of view for the secondary radiation detected.

The tray and transport housing 15 (see FIGS. 2 and 3) includes specimen and security covers, respectively at 36 and 37. The housing 15 contains a transport mechanism 38 to suitably position the specimens 57, including standards of known samples at the site of source 34 and detector 23.

The transport mechanism 38 includes a tray 40, transport 41, and a saddle 42 which defines smooth and threaded longitudinal holes 44, 45 respectively receiving a guide rail 46 and a drive screw 47, each being suitably mounted between the ends of the tray and transport housing 15. Suitable bellows 50 cover the guide rail 46 and drive screw 47 on both sides of the saddle 42, preventing accumulation of fuel or absorber materials including for example unacceptably abrasive uranium particles and dust.

The transport 41 includes built-in standards 52 shown permanently mounted in the transport 41 and defines a recess for inserting the tray 40 and the specimen that it holds, including known or unknown samples destined for analysis.

A suitable pulley 55 is suitably fixed onto the end of the driver screw 47, which is rotated by a suitable mounted stepper motor 56.

The tray 40 carries specimen 57 of known standards or unknown samples in suitable depressions 58 defined in its body. In view of the potential to automatically position specimen at the detector site in this invention, the depressions 58 can be placed at regular or irregular intervals along the surface of the tray 40.

The maximum number of specimens 57 that can be held by a single tray 40 is variable and is limited only by the size of the specimens 57. The specimen 57 examined may be a pellet or powder form. Packed powder pressed into a reasonably homogenous consistency is preferred to loose powder, since loose powder causes irregularities in the secondary radiation produced.

The parts of the transport mechanism 38 are preferably constructed of 304 stainless steel rather than 316 stainless steel which would produce undesirable secondary radiation interfering with secondary radiation from the nuclear fuel $UO_2$ and the absorber $Gd_2O_3$ employed in the preferred embodiment of this invention. Other materials of construction may be required when other primary and secondary materials are the desired object of analysis.

Proximity switches 60 and 61 tell whether the specimen and security covers respectively 36 and 37 are open or closed. Other proximity switches 62 and 63 respectively indicate the position of the tray at the beginning or end of its run in the tray and transport housing 15. Information regarding the state of each of these proximity switches is suitably provided along bit lines or buses 65 to the process controller system 67 as shown in FIG. 4.

Figure 4:
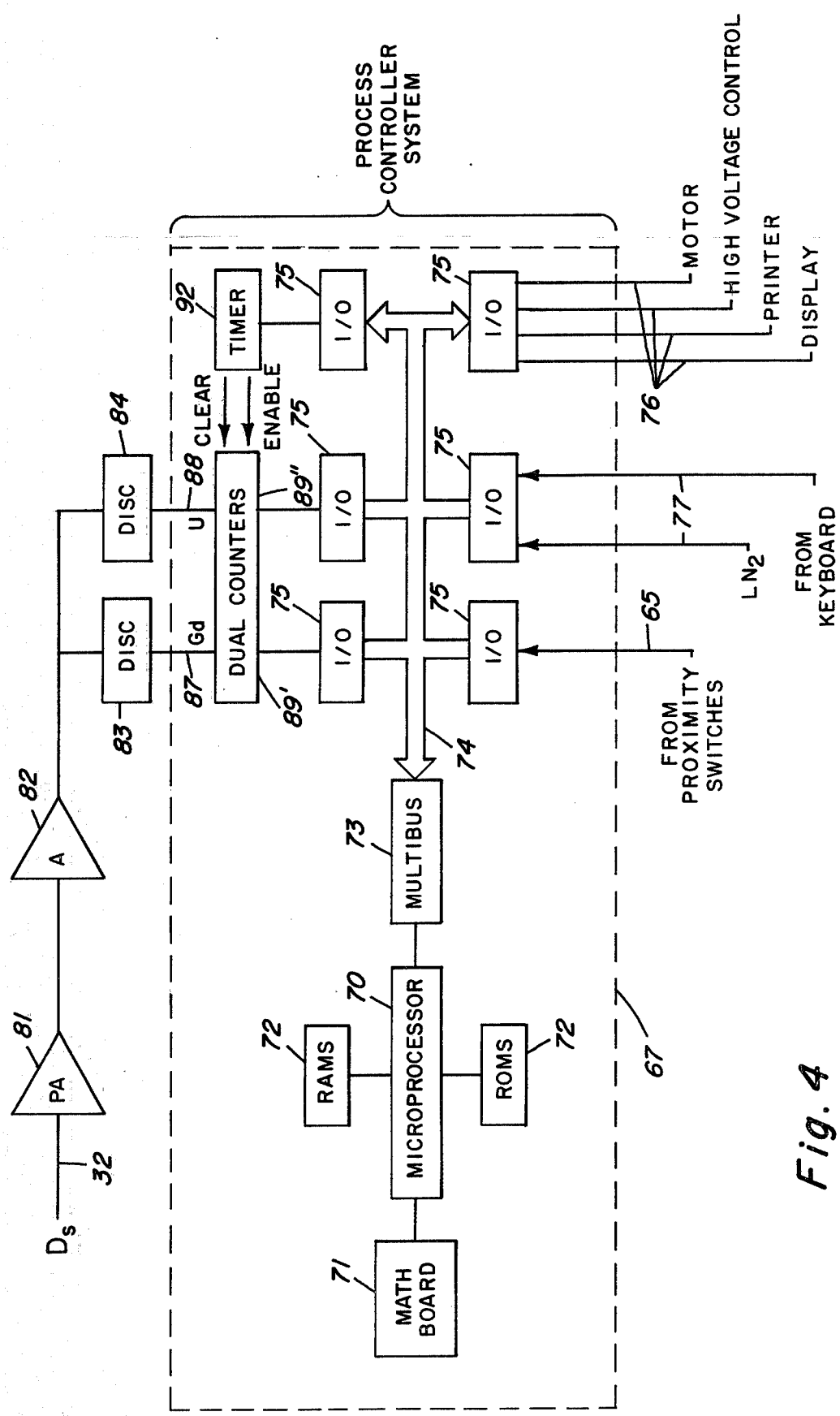
FIG. 4 is a schematic diagram showing the detector circuitry and the process controller subsystem of the analyzer.

The process controller system 67 in FIG. 4 preferably includes an Intel 8080 or equivalent microprocessor 70, a math board 71 for fast processing of information according to specialized operations, and associated memory devices 72 such as a suitable number of RAMs and ROMs. An Intel Multibus (TM) 73 oversees the manipulation of data with regard to a data bus 74 and controls the operation of various input/output devices 75, at least some of the latter for example being in the nature of 8255 Intel chips.

Plural bit lines or buses 76 control the operation of the analyzer including the stepper motor 56, the printer 17 (1), the status indicator 17 (2), the display 17 (3), the sonic alarm 17 (4), and the supply of high voltage to the detector crystal 23'. Other bit lines or buses 77 carry information from a liquid nitrogen sensor 27' in the dewar 21, and from the key board 18 to the process controller system 67.

Figure 5:
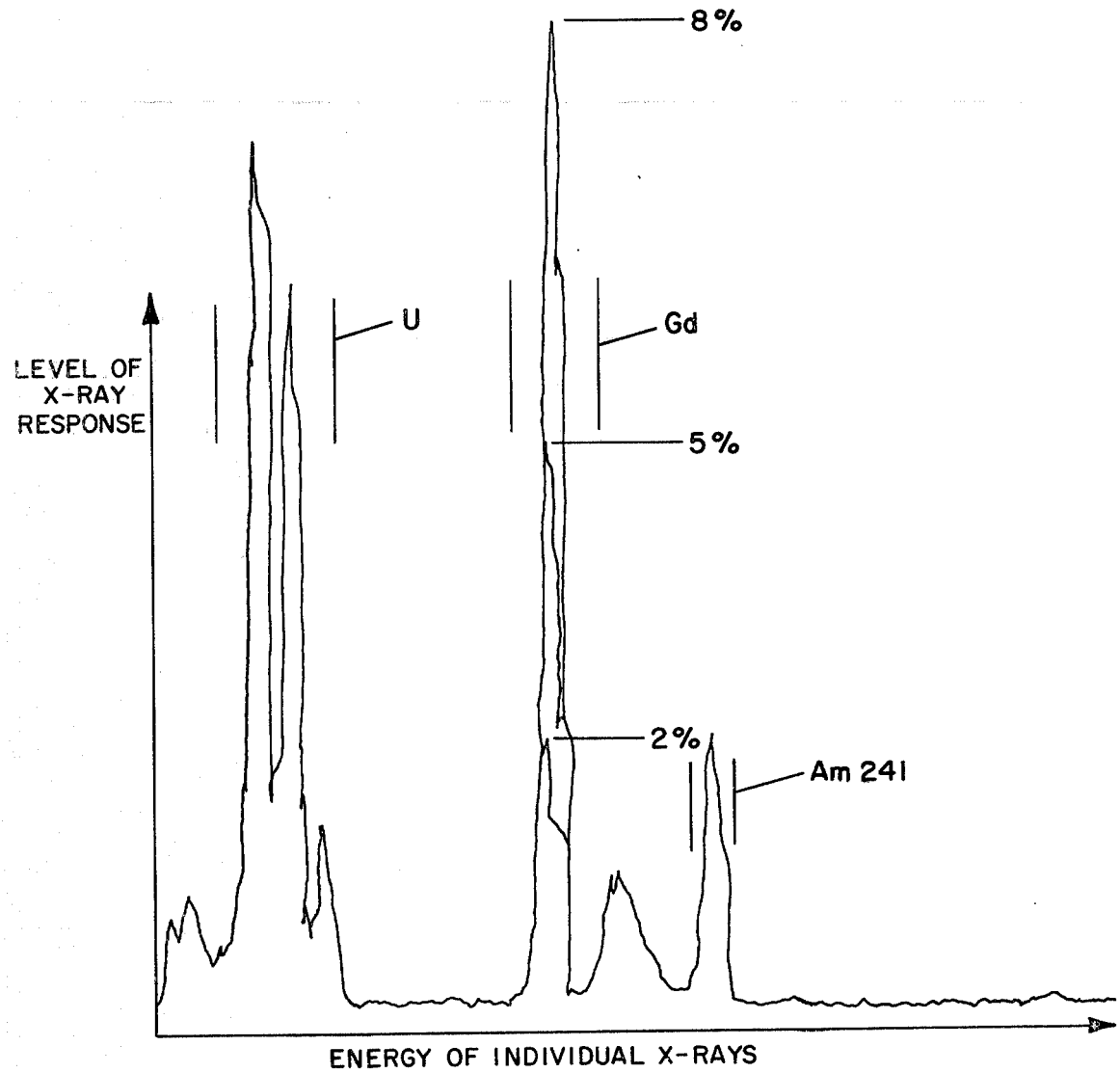
FIG. 5 is a graph of secondary x-ray response as a function of energy level of the x-ray detected.

As shown in FIG. 4, a detector signal 32 from the detector 23 indicates a rate of secondary radiation from the region exposed to primary radiation from source 34. This signal is fed to a preamplifier 81 and conditioned for receipt by an amplifier 82 magnifying the amplitude of the conditioned signal. Each of discriminators 83 and 84 receives the signal 80 in suitably conditioned and amplified form, which is then suitably filtered to produce two signals 87 and 88, respectively indicative, for example, of the rate of absorber source and the rate of fuel source secondary radiation. Each of the discriminators 83 and 84 is connected to a corresponding counter, respectively 89' and 89''. Each counter is suitably connected to associated timing circuitry 92 which sets the counting period, clears or initializes the counter, and "enables" the counter to begin counting. Each counter 89' or 89'' preferably has a capacity of 24 bits. As shown in FIG. 5, the respective discriminators 83 and 84 are responsive for example to x-ray signals between defined energy bands reflecting the uranium or gadolinium source of the x-rays.

Turning now to FIGS. 7 through 13 and in particular to the sequence of steps in FIG. 7 beginning with block 200, there is shown the operation of the analyzer including a number of preparatory steps establishing a calibration curve, checking calibration, and conducting sample analysis.

In particular, a sufficiently high level of liquid nitrogen is provided to the dewar 21 for cooling the detector crystal 23, as noted in block 202. When sufficiently cooled, high voltage for operating the detector can be applied, as indicated in block 203. The entire start-up procedure takes about four hours, including the time required for cooling the detector and allowing the system to stabilize (block 204).

The analyzer must be initialized prior to operation (block 201). This includes setting both counters 89' and 89" to zero, whereby the total at the end of a counting period accurately reflects the signal conducted.

Figure 6:
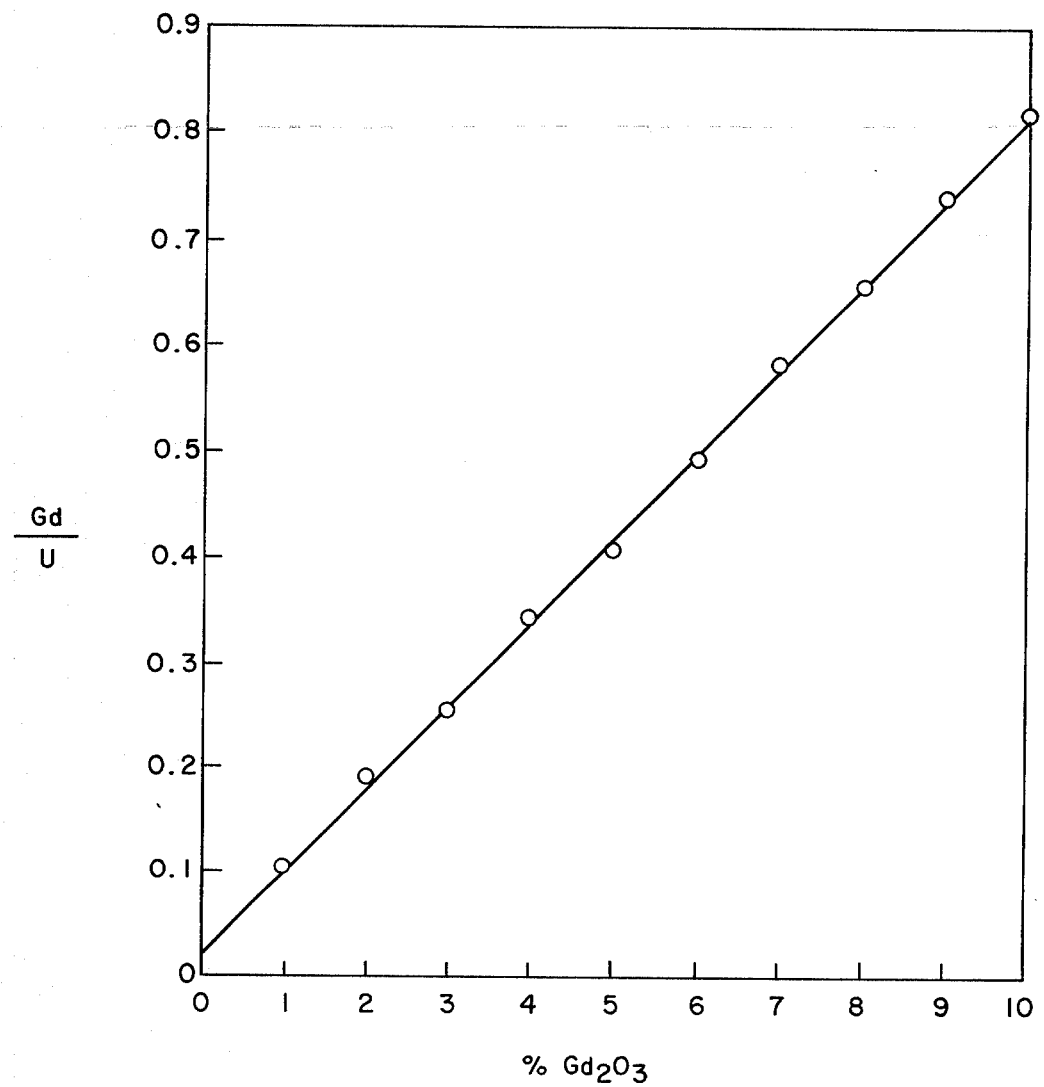
FIG. 6 shows a typical calibration curve.

Establishing a calibration curve relating the secondary material (in this case, gadolinium) to primary material (in this case, uranium) counts ratio to secondary material concentration follows next (block 210). Since the secondary material in the preferred embodiment is gadolinium (i.e., $Gd_2O_3$) and the primary material is uranium ($UO_2$) derived, it follows that the calibration curve sets forth the relationship between the gadolinium to uranium counts ratio and gadolinium concentration. FIG. 6 shows the calibration curve as being linear; accordingly, the curve can be represented in computer memory 72 as a slope and intercept.

"STANDBY" is the mode of operation following calibration in which the validity of the calibration curve is repeatedly checked (block 211). Instantaneous temperature conditions or other environmental factors may significantly modify detector performance. Accordingly, the prior established calibration curve may no longer be valid under current conditions.

Sample analysis is the ultimate purpose of the analyzer in which it determines the actual secondary material concentration values of unknown samples (block 212).

Two kinds of return paths may be taken when a defect or irregularity occurs in calibration, standby, or sample analysis: EXIT or OUT. The OUT return path is more drastic than EXIT, since OUT requires a four-hour startup period; EXIT merely reestablishes the calibration curve, a much shorter procedure. Accordingly, OUT is only taken when the high voltage has to be turned off and an extended period of time is required to cool the detector crystal 23'. Paths 214 return operation to step 210 in FIG. 7; paths 215 return to step 201 in order to supply liquid nitrogen sufficient to cool the detector crystal 23'. Path 216 returns operation to standby after operation.

Each of the steps of calibration, standby, and analysis requires the proper positioning or centering of the sample or standard specimens in question at the detector site (block 221). Subroutine CALCURVE in chart B includes such a positioning or centering feature. To establish a suitable calibration curve, the built-in standards 52 can be employed, or a standards tray may be inserted in the transport 41. According to a preferred embodiment, ten standards are used for calibration, covering the range of secondary material concentrations between 1 to 10 percent by weight.

To start operation, the tray is at the beginning of its run as indicated by proximity switch 62. Then each of the standards is individually positioned or centered at the detector site and examined. Such an examination includes establishing a secondary to primary material count ratio for each standard (block 222). Path 224 causes the process controller system to keep hunting for the next standard, unless a determination is made that all desired standards have been examined (block 223). If proximity switch 63 is encountered prior to handling all of the standards, the routine takes a suitable EXIT, noting that a possible error has been encountered.

After all of the standards have been examined and a secondary to primary material count ratio has been established for each of them, an analytical (preferably linear) expression is determined which represents the relationship between the ratios and the known secondary material concentration values of the standards (block 225). Having established a suitable calibration curve, a return (block 226) is made to the top of block 211 in chart A.

Figure 9:
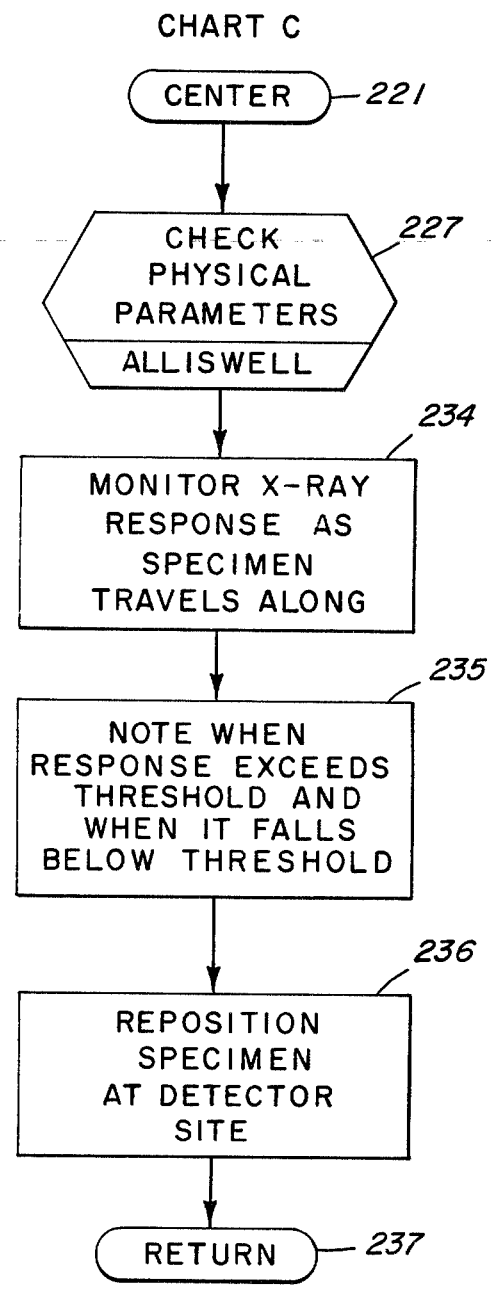
Figure 10:
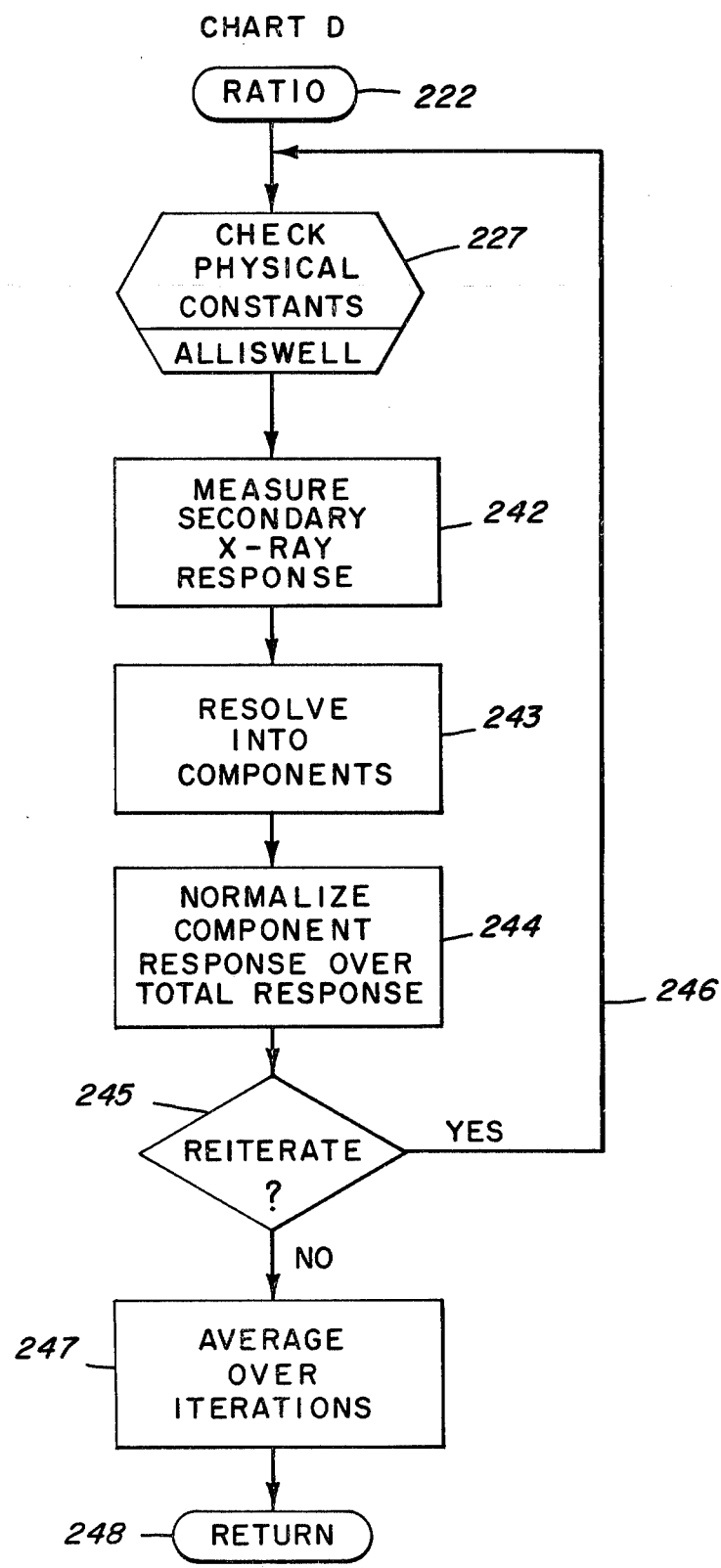
Figure 11:
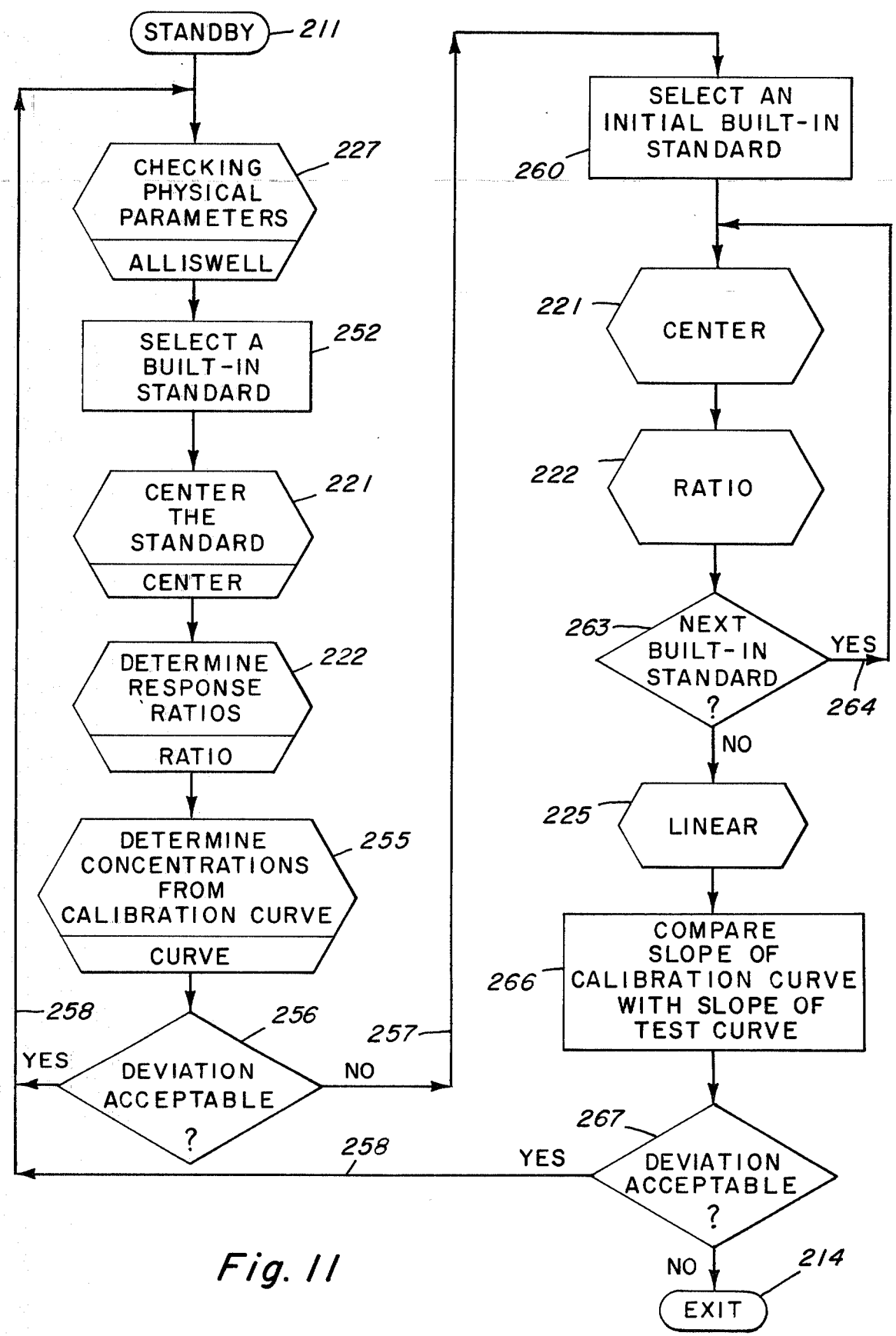

As shown in chart C of FIG. 9, each time centering is initiated (block 221), a check is conducted of selected physical parameters of the analyzer in the routine ALLISWELL (block 227). This is more particularly outlined in chart G of FIG. 13. Suffice it to say for now, however, that the check includes the conditions monitored by the proximity switches - relating to the position of the tray in the tray and transport housing. Additionally, the liquid nitrogen level is checked.

The detector repeatedly monitors the secondary radiation level as the stepper motor 56 drives the tray forward (block 234). The secondary radiation due to the primary and secondary material will rise and fall as each standard enters and departs from the detector site. In this embodiment, the process controller system 67 watches the primary material response level as each sample passes through the detector site. More specifically, the process controller system notes when the response rises above a preselected threshold value and when it recedes below that level (block 235). The time period between rising above and receding below the threshold reflects a distance traveled by the tray 40 between threshold points. For simplicity, centering is accomplished by reversing the direction of movement of the tray when the second threshold is reached and continuing in the reverse direction at about the same velocity as during forward motion for one-half the time between thresholds (block 236). This effectively insures that adequate centering or positioning has been accomplished. Control then returns to the top of block 222 in chart B through return block 237.

After centering has been accomplished, it is indicated to establish a secondary to primary material ratio for each standard according to the routine RATIO beginning with block 222 in chart D.

Aside from suitably positioning or centering each specimen at the detector site, the ratio of secondary material response is determined, as called for in the subroutine RATIO beginning with block 222 in chart D. Also, as suggested at block 227 in chart D, it is important to conduct a check of the physical parameters already discussed (e.g., closure of security and specimen covers 36, 37 and level of liquid nitrogen).

The secondary x-ray response is sensed by detector 23, as indicated at block 242. In the present embodiment, this involves a suitable counting period long enough to acceptably eliminate statistical error in the count. A possible time period is 16 seconds long, according to this embodiment.

The response is resolved (or discriminated) into source indicative components as suggested at block 243. This means that the secondary material source response rate is segregated from the primary material source response rate. Thereafter, the secondary material source response is normalized over the total source response to produce the desired secondary to primary material response ratio, as per block 244. As FIG. 5 shows, each discriminator 83 and 84 is effective within a selected energy band. Accordingly, one of the discriminators responds, for example, to Gd-source and the other to U-source signals.

In obtaining a secondary to primary material response ratio, it is frequently desirable to conduct more than a single count period for each specimen to be analyzed. Accordingly, multiple counts are foreseeable—in fact, as many as determined at decision block 245, which may direct control to proceed along path 246. Since only one ratio corresponding to each specimen is needed, provision is made for averaging (block 247) the multiple ratios established by reiteration along path 246, which produces a single representative ratio. Upon completion of the averaging, control returns to the calling routine block 248.

The x-ray fluorescence analyser is desirably available for analysis upon demand anytime of day or night. Accordingly, a period of "STANDBY" operation normally precedes sample analysis. The so-called STANDBY routine establishes the sequence of operation during this mode of activity beginning with block 211 in chart E in FIG. 11.

On STANDBY, the validity of the calibration curve is repeatedly evaluated. This involves both a cursory and a more comprehensive check, the comprehensive check occurring when the cursory check fails.

The cursive check in STANDBY begins, as do other subroutines discussed herein, with the usual check of physical parameters in block 227 according to the sequence established in the routine ALLISWELL.

A suitable built-in standard is selected (block 252) for the cursive check. Normally, this will be a standard in the high secondary material concentration range, since this will minimize statistical error. The selected standard is suitably positioned or centered as indicated at block 221. Thereafter, the standard is analyzed and a ratio representative of the standard is established (block 222). The actual secondary material concentration is determined by entering the calibration curve with the ratio established (block 255). If the deviation between the secondary material concentration determined and the known concentration value of the standard is unacceptably large (say for example over 3 percent), then the comprehensive check must be performed by following path 257. If the deviation is acceptable, however, the cursive check along path 258 is continually repeated.

The comprehensive check involves more than a single built-in standard, and preferably includes all of the built-in standards (block 260). Each of these standards is first suitably positioned or centered (block 221), and then analyzed to develop a secondary to primary material ratio (block 222) for as many standards as are established at block 263 which controls the return path 264.

The ratios thereby determined can be used to establish an analytical (preferably linear) relationship (block 225) between the ratios and secondary material concentration, much in the same manner as is involved in establishing a calibration curve in chart B. The slope of the relationship developed is compared with the slope of the calibration curve (block 266). If the deviation is unacceptable (block 267) an EXIT from STANDBY according to block 216 and as shown in FIG. 7 is performed. This causes the process controller subsystem to reestablish the calibration curve ab initio. If, however, the deviation is within acceptable limits, a return to the beginning of STANDBY along path 258 is made.

Figure 12:
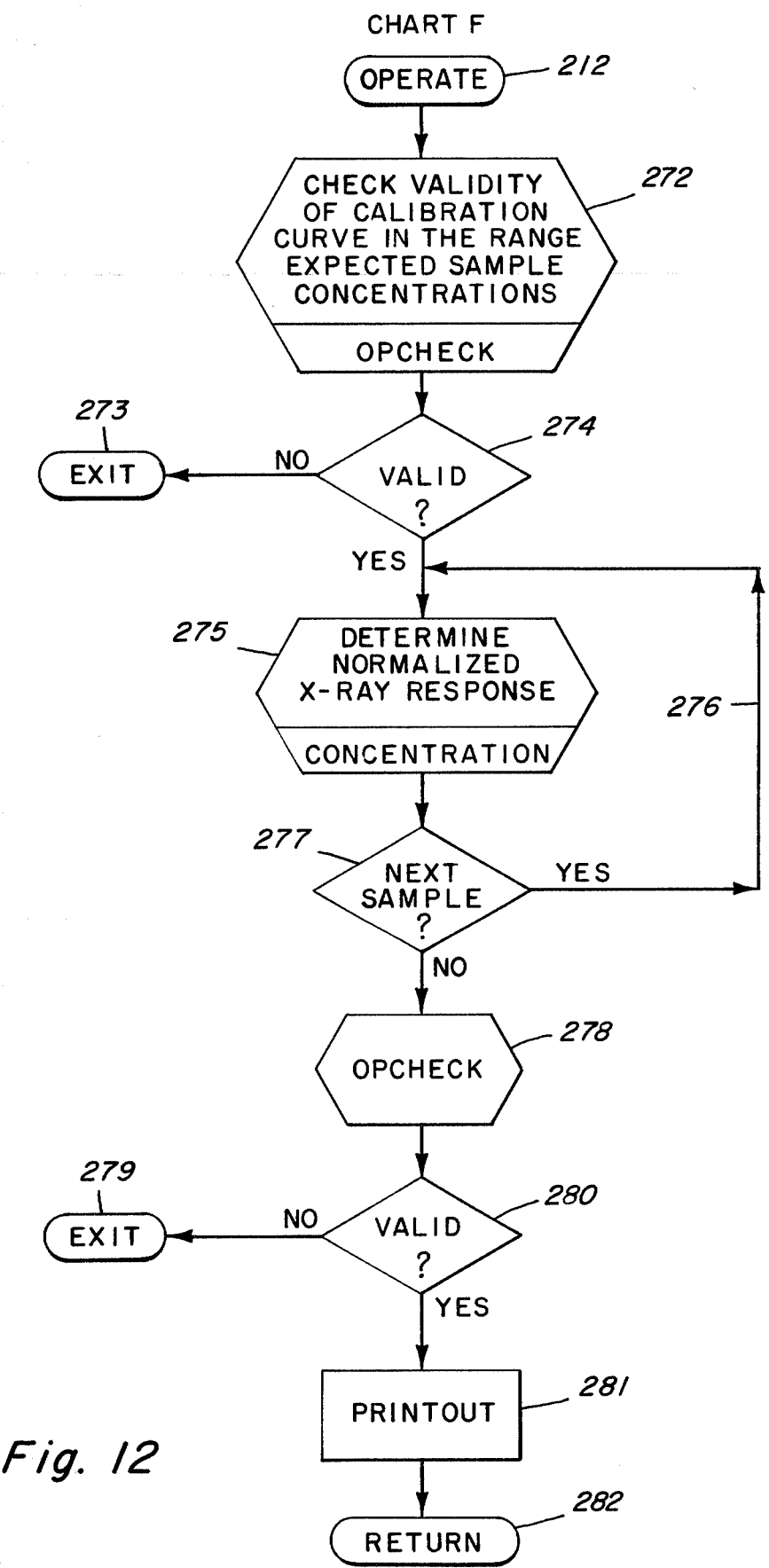

When sample analysis beginning with block 212 in chart F in FIG. 12 is desired (say after a period on STANDBY), a preliminary check of the validity of the calibration curve nearest the expected absorber concentration of the sample being analyzed is conducted (block 272). This is a check similar to the cursive check in STANDBY, since a single built-in standard is employed. The main difference is that the check is not necessarily conducted on a high secondary material concentration built-in standard, but instead involves the built-in standard closest in concentration value to the sample to be analyzed. This includes, as in prior cases, suitably positioning or centering the built-in standard selected, analyzing the standard, determining the secondary to primary material ratio involved, and then entering the calibration curve to determine the secondary material concentration value. If the deviation between the determined concentration value and the known concentration of the built-in standard used is unacceptable, either recalibration occurs immediately or another more comprehensive check is conducted to tell if recalibration is really necessary and whether the deviation can somehow still be considered to be within unacceptable range. In either case, EXIT (block 273) is effected if the calibration curve is considered invalid (block 274).

After this preliminary validity check of the calibration curve in the region of the sample concentration involved in the analysis has been conducted, the major steps of analysis (block 275) are performed. This includes (as usual) centering each of the specimens to be analyzed, sensing the secondary radiation from the region of the sample for a predetermined period of time, determining the ratio of secondary to primary material response, and then entering the calibration curve from which is determined the actual sample concentration for each of the samples under analysis. When each of the samples has been analyzed, the flow of operation no longer continues along path 276 from block 277 but instead proceeds to block 278 in order to conduct another validity check on the calibration curve which essentially repeats the check conducted at previous block 272. This is a useful check method, since it can be presumed that if the calibration curve was valid before and after the sample analysis, it must have been valid during analysis. If the check is not valid, however, the flow of operation departs from EXIT (block 279), through decision block 280. Otherwise, a printout of sample concentration values and other pertinent information is conducted from block 281. Then control returns to STANDBY through block 282.

Figure 13:
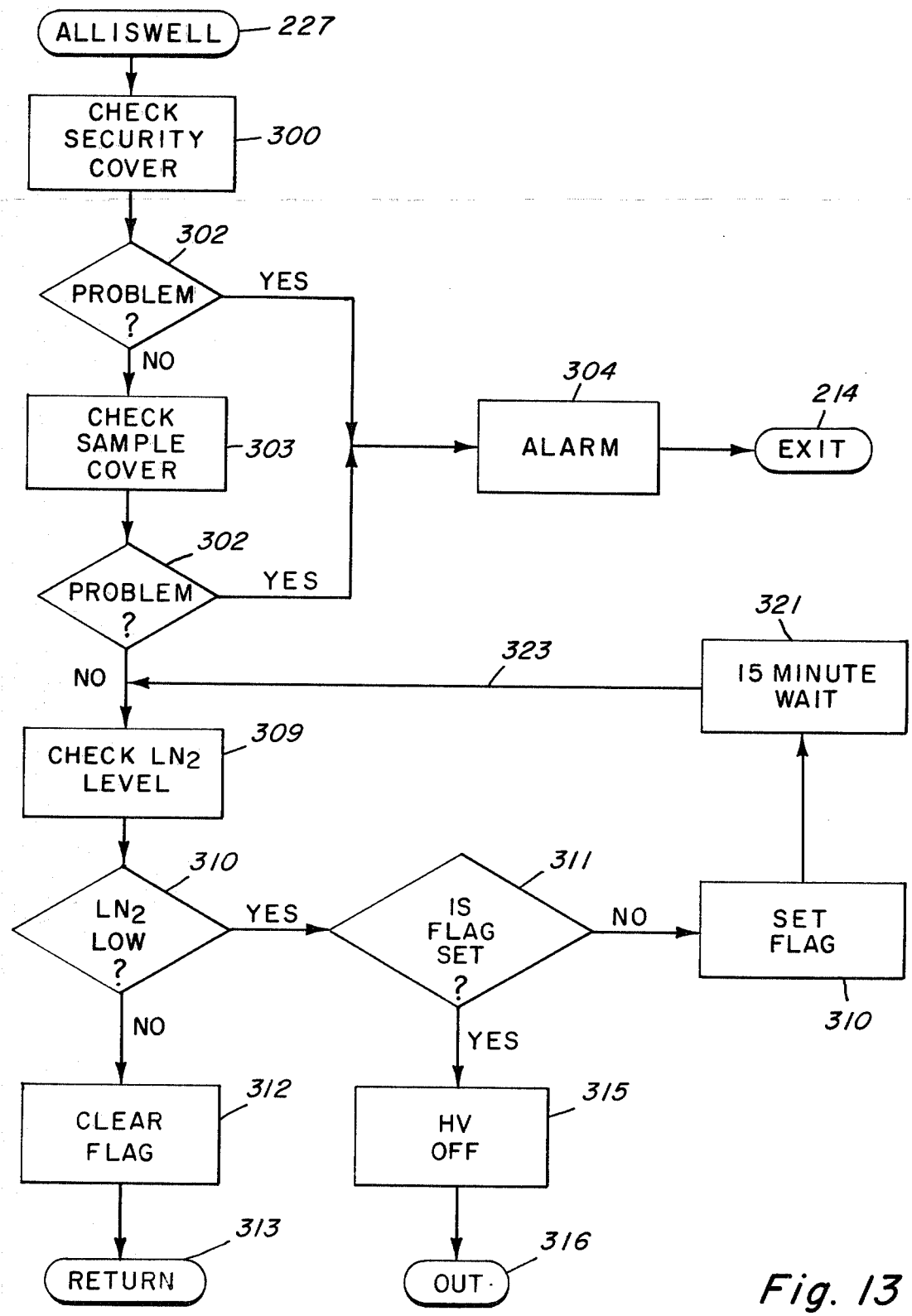

The routine for checking various physical parameters of the analyzer is shown in chart G in FIG. 13, beginning with block 272. In this routine, the security cover 37 is checked for closure (block 300). If it is open, decision block 302 directs an alarm 304 to sound and control passes through EXIT 214 as shown in chart A. If the security cover 37 is closed, the specimen cover 36 is checked for closure. As before, if the cover 36 is open, the alarm 304 is sounded and EXIT 214 is taken. Proximity switches 61 and 60 respectively indicate the closure state of the specimen and security covers 36, 37.

Next, the liquid nitrogen level is checked (block 309). If the liquid nitrogen level is too low (block 310) and an indication or flag already has been set (block 311), the high voltage to the detector is turned off (block 315), and control moves OUT 316 along path 315 shown in chart A. If, however, this is a first indication of low liquid nitrogen level, decision block 311 causes a flag to be set (block 310) and a delay (for example about 15 minutes long) is instituted (block 321) before rechecking the liquid nitrogen level. This provides a useful interval permitting the dewar to be refilled. However, if the level remains low the second time around the loop 323, the flag will have been set and OUT 316 will definitely be taken. If the liquid nitrogen is timely replenished, the flag will be cleared (block 312) and a RETURN 313 is taken to the calling routine.

To recapitulate, operating the analyzer includes establishing a calibration curve (block 210, FIG. 7) by examining known standard specimens and then analyzing unknown samples. Analysis of samples need not occur immediately after calibration; however, the analyzer must be continually available for use. Accordingly, it resides in STANDBY 211 until called to conduct analysis. STANDBY includes repeatedly checking the validity of the calibration curve.

In the instant embodiment, analysis is conducted by loading samples on try 40 to be inserted in a recess on the transport 41. During operation the tray 40 moves through the detector site exposing one sample at a time to primary radiation from the source 34. As each sample passes through the detector site, the secondary radiation sensed will rise above a threshold, level off, and then fall below the threshold again. This defines the width of the sample being analyzed and allows the stepper motor 56 to reposition the tray to suitably position or center the standard at the detector site.

Such centering occurs during calibration and during standby as well, only in such cases known standards rather than unknown samples are examined.

Once centering has been accomplished, a measure of the secondary radiation generated in the specimen being examined is conducted. The detector 23 produces an output signal indicative of the secondary radiation sensed; the discriminators 83, 84 resolve the signal into secondary material source and primary material source secondary radiation components (after signal conditioning and amplification has occurred); and the counters sum the rates of radiation over a specified counting period. A ratio of the secondary material source count and the primary material source count is established, and the ratio is used to produce an associated secondary material concentration value by comparison with the calibration curve.

The above description pertains to a single possible embodiment of the invention and its variations and is susceptible of reasonable modifications by those skilled in the art. However, this invention is not meant to be limited to the preferred embodiment shown and described. Rather the claims set forth the invention and are intended to cover all modifications coming within the spirit and scope of the embodiment described herein.

What is claimed is:

1. A method for analyzing at least one sample specimen comprising unknown concentrations of a primary material and at least a single secondary material by use of a radiation source, radiation detection means and a plurality of standard specimens, said standard specimens comprising known concentrations of said primary material and said at least single secondary material; said method including the steps of:
   (a) moving each of said plurality of standard specimens along a defined path into the vicinity of said radiation source such that each standard specimen in trun receives primary radiation effective to generate secondary radiation therefrom;
   (b) detecting said secondary radiation by producing a responsive electrical signal in said radiation detection means, said detection of said secondary radiation including the steps of determining for each of said plurality of standard specimens two threshold points along said defined path at which said secondary radiation rate begins and ceases, respectively, to exceed a predetermined threshold radiation rate and positioning each of said plurality of standard specimens at a point along said defined path substantially midway between said two threshold points such that a substantially maximized electrical signal is optained;
   (c) resolving said substantially maximized signal by means of frequency discrimination into component signals representative of respective secondary radiation rates fluoresced by said primary and secondary materials;
   (d) deriving a ratio for each standard specimen of a count of the secondary radiation derived from said at least one secondary material to a count of the secondary radiation derived from said primary material;
   (e) establishing a calibration curve for said plurality of standard specimens plotting the ratio for each standard specimen versus their secondary material concentration values;
   (f) examining said at least one sample specimen in analogous manner to said standard specimens and deriving a ratio of a count of the secondary radiation derived from said at least one secondary material to a count of the secondary radiation derived from said primary material for said at least one sample specimen; and
   (g) comparing said ratio of said sample specimen to said calibration curve to determine the secondary material concentration value of said sample specimen.

2. The method of claim 1, said method further including the steps of:
   reexamining at least one of said standard specimens by repeating steps (a)–(d) and comparing the ratio derived therefrom to said calibration curve to check the continued accuracy of the curve;
   reexaming said plurality of standard specimens by repeating steps (a)–(d) whenever said derived secondary material concentration value for said at least one reexamined standard specimen deviates from the established calibration curve by a selected deviation limit; and
   establishing at least a single new calibration curve plotting the corresponding at least single ratio versus the secondary material concentration values for said plurality of standard specimens.

3. A method for analyzing a sample specimen by use of a radiation source and radiation detection means, said sample specimen comprising a primary material and at least a single secondary material; said method including the steps of:

directing primary radiation toward said specimen to thereby cause said primary and secondary material in said sample specimen to generate secondary radiation;

detecting said secondary radiation by producing a responsive electrical signal in said radiation detection means, said detection of secondary radiation including the steps of positioning said sample specimen at a point substantially midway between two threshold points of a selected detected radiation rate such that a substantially maximized electrical signal is obtained;

resolving said substantially maximized signal by means of frequency discrimination into component signals representative of respective secondary radiation rates of said primary and secondary materials;

deriving a ratio of a count of the secondary radiation derived from said at least one secondary material to a count of the secondary radiation derived from said primary material;

and determining at least a single secondary material concentration value from said ratio.

4. The method of claim 3 and further including the steps of:

examining a plurality of standard specimens comprising known concentrations of said primary and said at least one secondary material; and comparing said ratio to said known concentration value of said at least one secondary material for each of said standard specimens to establish a calibration curve.

5. The method of claim 4 and further including the steps of:

examining a plurality of sample specimens comprising unknown concentrations of said primary and secondary materials;

determining material concentration values by comparing said ratio for said plurality of sample specimens with said calibration curve.

6. The method of claim 5, wherein said primary material includes uranium, and said at least single secondary material includes gadolinium.

7. The method of claim 1 or 3 wherein said primary material includes nuclear fuel.

8. The method of claim 1 or 3 wherein said primary material includes uranium.

9. The method of claim 1 or 3 wherein said secondary material includes neutron absorber material.

10. The method of claim 1 or 3 wherein said secondary material includes gadolinium.

11. The method of claim 1 or 3 wherein said secondary radiation comprises x-rays.

12. Apparatus for analyzing sample specimens comprising unknown relative quantities of a primary material and at least one secondary material; said apparatus comprising:

a source of radiation adapted to cause each of said specimens subjected thereto to fluoresce secondary radiation from said primary and secondary materials;

radiation detection means responsive to said fluoresced secondary radiation to generate an electrical signal indicative of the rate of said secondary radiation;

a plurality of standard specimens having known relative quantities of said primary and secondary materials;

transport means adapted to convey each of said sample specimens and said plurality of standard specimens along a defined path to an area near said radiation source wherein said secondary radiation rate exceeds a predetermined threshold;

means for positioning each of said specimens in said area midway between the points along said defined path at which said secondary radiation begins and ceases respectively to exceed said predetermined threshold;

signal discriminating means for resolving said electrical signal into component signals representative of respective radiation rates fluoresced by said primary and secondary materials; and means for developing a ratio from said component signals for each of said specimens of a count of said secondary material derived secondary radiation to a count of said primary material derived secondary radiation;

whereby said plurality of standard specimens may be used to establish at least a single calibration curve which plots one of said ratios against the concentration value of said secondary material, and said sample specimens may be analyzed in analogous manner to said standard specimens to produce at least a single secondary material concentration value by comparison of the ratio of each of said sample specimens with said calibration curve.

13. The apparatus of claim 12, wherein said source of radiation comprises a radioisotope.

14. The apparatus of claim 12, wherein a portion of said specimen are standards of known gadolinium concentration value and the remainder of said specimen are unknown samples, said known standards are employed to establish a calibration curve of the gadolinium to uranium ratios versus gadolinium concentration, and said unknown samples produce other gadolinium to uranium ratios permitting the entry of said calibration curve for extracting a gadolinium concentration value for each of said unknown samples.

15. Apparatus for analyzing sample specimens comprising unknown relative quantities of a primary material and at least one secondary material; said apparatus comprising:

a source of radiation adapted to cause each of said specimens subjected thereto fluoresce secondary radiation from said primary and secondary materials;

radiation detection means responsive to said fluoresced secondary radiation to generate an electrical signal indicative of the rate of said secondary radiation;

signal discrimination means for resolving said electrical signals into component signals representative of respective radiation rates fluoresced by said primary and secondary materials;

a plurality of standard specimens having known relative quantities of said primary and secondary materials;

transport means adapted to convey each of said sample specimens and said plurality of standard specimens at a substantially constant speed in a first direction of travel along a defined path to and through an area near said radiation source wherein said primary material secondary radiation rate exceeds a predetermined threshold;

means for determining the duration of a transit time period for each of said sample and standard specimens in said area as each is conveyed through said area;

said transport means being further adapted to convey each of said sample specimens and said standard specimens into said area in a second direction along said path at said substantially constant speed for a time period equal in duration to one half the duration of said transit time period whereby each of said specimens can be positioned substantially midway between two points at which said primary material secondary radiation begins and ceases respectively to exceed said predetermined threshold; and means for developing a ratio for each of said specimens from a count of said secondary radiation rate derived from said secondary material compared to a count of said secondary radiation rate derived from said primary material;

whereby said plurality of standard specimens may be used to establish at least a single calibration curve which plots one of said ratios against the concentration value of said secondary material, and said sample specimens may be analyzed in analogous manner to said standard specimens to produce at least a single secondary material concentration value by comparison of the ratio of each of said sample specimens with said calibration curve.

* * * * *